United States Patent
Skaria et al.

(10) Patent No.: US 9,956,314 B2
(45) Date of Patent: May 1, 2018

(54) ADHESIVE FOR USE WITH BONE AND BONE-LIKE STRUCTURES

(71) Applicant: Modern Ideas LLC, Watertown, MA (US)

(72) Inventors: Sunny Skaria, Concord, MA (US); Kenneth Berk, Newton, MA (US)

(73) Assignee: Modern Ideas LLC, Watertown, MA (US)

( * ) Notice: Subject to any disclaimer, the term of this patent is extended or adjusted under 35 U.S.C. 154(b) by 0 days. days.

(21) Appl. No.: 15/006,228

(22) Filed: Jan. 26, 2016

(65) Prior Publication Data

US 2017/0209617 A1 Jul. 27, 2017

(51) Int. Cl.
| | |
|---|---|
| A61L 24/06 | (2006.01) |
| A61L 24/00 | (2006.01) |
| A61K 6/00 | (2006.01) |
| A61K 6/083 | (2006.01) |
| A61L 24/04 | (2006.01) |

(52) U.S. Cl.
CPC ............ *A61L 24/06* (2013.01); *A61K 6/0017* (2013.01); *A61K 6/0023* (2013.01); *A61K 6/0047* (2013.01); *A61K 6/0082* (2013.01); *A61K 6/0091* (2013.01); *A61K 6/0835* (2013.01); *A61L 24/0089* (2013.01); *A61L 24/0094* (2013.01); *A61L 24/043* (2013.01)

(58) Field of Classification Search
None
See application file for complete search history.

(56) References Cited

U.S. PATENT DOCUMENTS

| | | | |
|---|---|---|---|
| 4,806,381 | A | 2/1989 | Engelbrecht et al. |
| 4,849,193 | A | 7/1989 | Palmer et al. |
| 4,872,936 | A | 10/1989 | Engelbrecht |
| RE33,161 | E | 2/1990 | Brown et al. |
| RE33,221 | E | 5/1990 | Brown et al. |
| 5,037,639 | A | 8/1991 | Tung |
| 5,238,491 | A | 8/1993 | Sugihara et al. |
| 5,460,803 | A | 10/1995 | Tung |
| 5,508,342 | A | 4/1996 | Antonucci et al. |
| 5,522,893 | A | 6/1996 | Chow et al. |
| 5,650,176 | A | 7/1997 | Lee et al. |
| 5,676,976 | A | 10/1997 | Lee et al. |
| 5,708,052 | A | 1/1998 | Fischer et al. |
| 6,024,985 | A | 2/2000 | Simkiss et al. |
| 6,056,930 | A | 5/2000 | Tung |
| 6,114,408 | A | 9/2000 | Dickens |
| 6,214,368 | B1 | 4/2001 | Lee et al. |
| 6,245,872 | B1 | 6/2001 | Frey et al. |
| 6,325,992 | B1 | 12/2001 | Chow et al. |
| 6,649,669 | B2 | 11/2003 | Dickens |
| 7,041,709 | B2 | 5/2006 | Klee et al. |
| 7,091,260 | B2 | 8/2006 | Kuhn |
| 7,189,263 | B2 | 3/2007 | Erbe et al. |
| 7,449,499 | B2 | 11/2008 | Craig et al. |
| 7,491,694 | B2 | 2/2009 | Reynolds et al. |
| 7,727,539 | B2 | 6/2010 | Laurencin et al. |
| 7,758,693 | B2 | 7/2010 | Wenz |
| 7,767,731 | B2 | 8/2010 | Chen et al. |
| 7,879,388 | B2 | 2/2011 | Clarkson et al. |
| 7,879,924 | B2 | 2/2011 | Torii et al. |
| 8,158,694 | B2 | 4/2012 | Tanaka et al. |
| 8,216,359 | B2 | 7/2012 | Lee et al. |
| 8,221,781 | B2 | 7/2012 | Rosenberg et al. |
| 8,263,048 | B2 | 9/2012 | Yang et al. |
| 8,282,396 | B2 | 10/2012 | Chow et al. |
| 8,303,967 | B2 | 11/2012 | Clineff et al. |
| 8,440,741 | B2 | 5/2013 | Sang et al. |
| 8,497,312 | B2 | 7/2013 | Matsushige et al. |
| 8,545,858 | B2 | 10/2013 | Rosenberg et al. |
| 8,551,525 | B2 | 10/2013 | Cook et al. |
| 8,557,038 | B2 | 10/2013 | Chow et al. |
| 8,609,071 | B2 | 12/2013 | Reynolds |
| 8,710,114 | B2 | 4/2014 | Rusin et al. |

(Continued)

FOREIGN PATENT DOCUMENTS

| | | |
|---|---|---|
| EP | 2123246 A1 | 11/2009 |
| EP | 2305205 A1 | 4/2011 |

(Continued)

OTHER PUBLICATIONS

Chen, Liang et al., "Bioactive dental restorative materials: A review," American Journal of Dentistry, vol. 26, No. 4, pp. 219-227, Aug. 2013.
Al-Sanabani, Jabr S. et al., "Application of Calcium Phosphate Materials in Dentistry," International Journal of Biomaterials, vol. 2013, Article ID 876132, 19 pages, May 2013.
Spencer, Paulette et al., "Adhesive/Dentin Interface: The Weak Link in the Composite Restoration," Ann Biomed Eng., vol. 38, No. 6, 1989-2003, 24 pages, Jun. 2010.
Arsad et al., "Synthesis and Characterization of Hydroxyapatite Nanoparticles and β-TCP Particles," 2011 2nd International Conference on Biotechnology and Food Science, IPCBEE, vol. 7, pp. 184-188, 2011.
Chen et al. "Bond Strengths of Two Self-ashesive Resin Cements to Dentin with Different Treatments," Journal of Medical and Biological Engineering, vol. 31, No. 1, pp. 73-77, 2011.

(Continued)

*Primary Examiner* — Sanza Mcclendon
(74) *Attorney, Agent, or Firm* — Sunstein Kann Murphy & Timbers LLP (57) ABSTRACT

An adhesive composition for bonding to bone and bone-like structures includes a polymerizable, multifunctional acidic monomer having a concentration ranging from about 5% to about 45% by weight of the adhesive composition, one or more multifunctional monomers with one or more ethylenically unsaturated groups having a concentration ranging from about 20% to about 60% by weight of the adhesive composition, an organically modified calcium phosphate salt with one or more pendant polymerizable groups having a concentration ranging from about 1% to about 50% by weight of the adhesive composition, and a polymerization initiator system. A method of forming the adhesive composition is also provided.

23 Claims, 4 Drawing Sheets

(56) References Cited

U.S. PATENT DOCUMENTS

| | | | |
|---|---|---|---|
| 8,728,536 | B2 | 5/2014 | Lee et al. |
| 8,796,354 | B2 | 8/2014 | Gyakushi et al. |
| 8,871,167 | B2 | 10/2014 | Aizawa et al. |
| 8,889,196 | B2 | 11/2014 | Xu |
| 8,957,126 | B2 | 2/2015 | Rusin et al. |
| 2003/0071387 | A1 | 4/2003 | Beitelshees et al. |
| 2006/0004122 | A1 | 1/2006 | Hecht et al. |
| 2006/0240121 | A1 | 10/2006 | Lee et al. |
| 2007/0184035 | A1 | 8/2007 | Pugh et al. |
| 2008/0318190 | A1 | 12/2008 | Suh et al. |
| 2014/0050674 | A1 | 2/2014 | Tjaderhane |
| 2014/0079650 | A1 | 3/2014 | Reynolds |
| 2016/0256362 | A1 | 9/2016 | Skaria et al. |

FOREIGN PATENT DOCUMENTS

| | | | |
|---|---|---|---|
| JP | 2009084200 | A | 4/2009 |
| JP | 2012077009 | A * | 4/2012 |
| WO | 9836639 | A1 | 8/1998 |
| WO | 0247572 | A1 | 6/2002 |
| WO | 2010033515 | A1 | 3/2010 |

OTHER PUBLICATIONS

Constantz et al., "Skeletal Repair by in Situ Formation of the Mineral Phase of Bone," Science, vol. 267, pp. 1796-1799, Mar. 24, 1995.

Dhanalakshmi et al., "Synthesis and preliminary characterization of polyethylene glycol (PEG)/hydroxyapatite (HAp) nanocomposite for biomedical applications," International Journal of Physical Science, vol. 7, No. 13, pp. 2093-2101, Mar. 23, 2012.

Dorozhkin, "Amorphous Calcium Orthophosphates: Nature, Chemistry and Biomedical Applications," International Journal of Materials and Chemistry, vol. 2, No. 1, pp. 19-46, 2012.

Drouet, "Apatite Formation: Why It May Not Work as Planned, and How to Conclusively Identify Apatite Compounds," Hindawi Publishing Corporation, BioMed Research International, vol. 2013, Article ID 490946, 12 pages, 2013.

Goncalves et al., "Dental cementum reviewed: development, structure, composition, regeneration and potential functions," Braz. J. Oral. Sci., vol. 4, No. 12, pp. 651-658, Jan./Mar. 2005.

Goudouri et al., "In Vitro Bioactivity Studies of Sol-Gel Derived Dental Ceramics/Bioactive Glass Composites in Periodically Renewed Biomimetic Solution," Ashdin Publishing, Bioceramics Development and Applications, vol. 1, Article ID D110250, 4 pages, 2011.

Grover et al., "In vitro ageing of brushite calcium phosphate cement," Biomaterials, vol. 24, pp. 4133-4141, 2003.

Grover et al., "The effect of amorphous pyrophosphate on calcium phosphate cement resorption and bone generation," Biomaterials, vol. 34, pp. 6631-6637, 2013.

Huang et al., "In vivo evaluation of poorly crystalline hydroxyapatite-based biphasic calcium phosphate bone substitutes for treating dental bony defects," J. Dent. Sci., vol. 5, No. 2, pp. 100-108, 2010.

Idrissi et al., "A novel method of synthesize nanocrystalline hydroxyapatite: Characterization with x-ray diffraction and infrared spectroscopy," IOSR Journal of Applied Chemistry, vol. 7, Issue 5, Ver. III, pp. 107-112, May 2014.

Jefferies, "Advances in Remineralization for Early Carious Lesions: A Comprehensive Review," Continuing Education 1, Compendium, vol. 35, No. 1, 7 pages, Jan. 2014.

Kantharia et al., "Nano-hydroxyapatite and its contemporary applications," Journal of Dental Research and Scientific Development, vol. 1, Issue 1, pp. 15-19, 2014.

Oortgiesen et al., "Regeneration of the periodontium using enamel matrix derivative in combination with an injectable bone cement," Clin.Oral. Invest., vol. 17, pp. 411-421, 2013.

Sun et al., "Preparation and Properties of Nanoparticles of Calcium Phosphates With Various Ca/P Ratios," Journal of Research of the National Institute of Standards and Technology, vol. 115, No. 4, pp. 243-255, 2010.

Tomsia et al., "Biomimetic Bonelike Composites and Novel Bioactive Glass Coatings," Advanced Engineering Materials, vol. 7, No. 11, pp. 999-1004, 2005.

Tseng et al., "Polymer-assisted synthesis of hydroxyapatite nanoparticle," Materials Science and Engineering C, vol. 29, pp. 819-822, 2009.

Zhao et al., "Amorphous calcium phosphate and its application in dentistry," Chemistry Central Journal, vol. 5, No. 40, 7 pages, 2011.

International Searching Authority, International Search Report-International Application No. PCT/US2016/017255, dated Apr. 28, 2016, together with the Written Opinion of the International Searching Authority, 12 pages.

International Search Report—International Application No. PCT/US2017/014502, dated May 9, 2017 together with the Written Opinion of the International Searching Authority, 16 pages.

* cited by examiner

ADHESIVE FOR USE WITH BONE AND BONE-LIKE STRUCTURES

TECHNICAL FIELD

The present invention relates to adhesives, and more specifically to adhesives suitable for use with bone and bone-like structures in dental and biomedical applications.

BACKGROUND ART

In recent years, dental adhesive chemistry has seen much progress. It has advanced from a multi-component, multi-step process to a single-component, single-step process. In the past, there was a phosphoric acid etch step followed by a dental adhesive which infiltrated the dentinal tubules with a polymerizable resin carried into the dentinal tubules by a hydrophilic solvent such as ethanol or acetone. This adhesive layer was light polymerized, and a composite restoration was then placed on top of the adhesive and cured. This process resulted in a micro-mechanical attachment between the tooth and the restorative material. More recently, adhesive systems have been developed in which the phosphoric acid etch step has been eliminated. Phosphate-containing acid-monomers in an azeotropic solvent of ethanol and/or acetone with water have been used as a bond material. The acid monomers reduce the pH to a level suitable for etching and the azeotrope carries the polymerizable resin into the dentinal tubules. The material relies on micro-mechanical attachment, the association of like moieties for tooth integration, and the presence of phosphate ions to form a chemical bond to calcium ions in the tooth.

Calcium containing cements have been used as structural supports in orthopedic and dental applications. Recently, biologically active restorative materials were developed that may stimulate the repair of tooth structure through the release of cavity-fighting components including calcium and phosphate. The use of amorphous calcium phosphate (ACP) was disclosed as a bioactive filler encapsulated in a polymer binder. Calcium and phosphate ions released from ACP composites, especially in response to changes in the oral environment caused by bacterial plaque or acidic foods, can be deposited into the tooth structures as an apatite mineral, which is similar to the hydroxyapatite found naturally in teeth. The ACP has the properties of both a preventive and restorative material. This encourages its use in dental cements, sealants, composites, and, more recently, orthodontic adhesives. Though ACP has been used in some dental applications, its use in dental restorative materials is very limited due to its stability. In contact with water, ACP turns into hydroxyapatites. Another drawback of calcium phosphate cement is its low mechanical properties. Hydroxyapatite as a bulk solid does not have the necessary mechanical properties, such as strength or stiffness, to be used in load bearing applications. While much has been learned about the structure and growth of bone tissue due to modern microscopy, no reliable method of synthesizing this structure has been developed.

SUMMARY OF EMBODIMENTS

In accordance with one embodiment of the invention, an adhesive composition for bonding to bone and bone-like structures includes a polymerizable, multifunctional acidic monomer having a concentration ranging from about 5% to about 45% by weight of the adhesive composition, one or more multifunctional monomers with one or more ethylenically unsaturated groups, the one or more multifunctional monomers having a concentration ranging from about 20% to about 60% by weight of the adhesive composition, an organically modified calcium phosphate salt having a concentration ranging from about 1% to about 50% by weight of the adhesive composition and having one or more pendant polymerizable groups, and a polymerization initiator system.

In some embodiments, the multifunctional acid monomer may be bis[2-(methacryloyloxy)ethyl] phosphate, glycerol dimethacrylate phosphate, ethylene glycol methacrylate phosphate, polyethylene glycol methacrylate phosphate, 2-Acrylamido-2-methylpropanephosphonic acid, methacryloyloxy decyl hydrogen phosphate, methacryloyloxy ethyloxy phosphate, and/or 10-methacryloyloxydecyl dihydrogen phosphate. The organically modified calcium phosphate salt may have a concentration ranging from 5% to about 30% by weight of the adhesive composition. The organically modified calcium phosphate salt may be completely soluble in the adhesive composition. The organically modified calcium phosphate salt may be stabilized by a reaction of a calcium salt and an organically functional phosphate monomer having at least one polymerizable group. The organically functional phosphate monomer may be bis[2-(methacryloyloxy)ethyl] phosphate and/or vinyl phosphonic acid. The adhesive composition may further include a non-acidic monomer having a concentration ranging from about 20% to about 60% by weight of the adhesive composition. The polymerization initiator system may have a concentration ranging from about 0.1% to about 4% by weight. The polymerization initiator system may include a photo-polymerization initiator having a concentration ranging from about 0.25% to about 3% by weight of the adhesive composition. The adhesive composition may further include a volatile organic solvent having a concentration ranging from about 0.1% to about 40% by weight of the adhesive composition. The adhesive composition may further include one or more inert fillers, such as glass, quartz, and/or silica. The adhesive composition may further include one or more non-polymerizable, polymeric fillers configured to allow debonding of the adhesive component on-demand. The one or more non-polymerizable, polymeric fillers may be polyvinylidene difluoride, cellulose acetate, cellulose acetate propionate, and/or cellulose acetate butyrate. Embodiments may include a method of forming the adhesive composition.

BRIEF DESCRIPTION OF THE DRAWINGS

The foregoing features of the invention will be more readily understood by reference to the following detailed description, taken with reference to the accompanying drawings, in which.

DESCRIPTION OF ILLUSTRATIVE EMBODIMENTS

Embodiments of the present invention provide an actinically polymerizable adhesive composition suitable for adhesion to bone and bone-like substrates, e.g., teeth and nails. The adhesive composition includes stabilized calcium phosphate salts with pendant methacrylate groups that have the ability to take part in actinic polymerization. The adhesive composition further includes an acidic monomer and one or more multifunctional monomers and can polymerize to form an adhesive material having good adhesion to dentin and other bone-like substrates with an adhesive shear bond strength of at least 8 MPa. The adhesive composition may be used with or without an etchant and may include thickeners and aesthetic enhancers depending on the requirements of a particular use. The adhesive composition preferably includes initiators, accelerators and/or inhibitors to enable light curing. The adhesive composition is formulated as a single component material. Embodiments include modified calcium and phosphate moieties and are storage stable for periods up to 24 months or longer in the temperature range of 0° C. to 60° C. The adhesive composition includes no acetone, ethanol or other volatile solvent.

It is believed that embodiments of the adhesive composition have a chemical bond between the tooth and the adhesive material through ionic linkage involving calcium and phosphate ions in the tooth and calcium and phosphate ions in the bond material, that has been stabilized with pendant methacrylate groups. Embodiments of the adhesive composition provide advantages over other dental and medical adhesives, such as the elimination of packaging issues and expenses caused by the need to protect against evaporation, elimination of tooth sensitivity caused by insufficient removal of volatile solvents, elimination of bond porosities caused by evaporation of volatile solvents, and elimination of the uncertainty faced by dental professionals in trying to decide when the volatile solvents have been fully eliminated. Details of illustrative embodiments are discussed below.

Embodiments of the present invention disclose adhesive compositions for bonding to bone and bone-like structures and methods of making same. The adhesive composition includes an organically modified calcium phosphate salt having a concentration ranging from about 1% to about 50% by weight of the adhesive composition and having one or more pendant polymerizable groups. The formation of a modified calcium phosphate according to embodiments of the present invention is described in U.S. patent application Ser. No. 14/638,289, which is incorporated by reference herein in its entirety. The adhesive composition further includes a polymerizable, multifunctional acidic monomer having a concentration ranging from about 5% to about 45% by weight of the adhesive composition. Preferably, the acidic monomer is bis[2-(methacryloyloxy)ethyl] phosphate (sometimes referred to hereafter as "Bis-2"), CAS #32435-46-4, a phosphate containing methacrylate ester reagent. The adhesive composition further includes at least one multifunctional monomer having one or more ethylenically unsaturated groups, preferably having at least two ethylenically unsaturated groups, and having a concentration ranging from about 20% to about 60% by weight of the adhesive composition. The adhesive composition further includes a polymerization initiator system, preferably in the range of about 0.1% to about 3% by weight of the adhesive composition. Before curing, the adhesive composition preferably has a pH of about 1-4.

Figure 1:
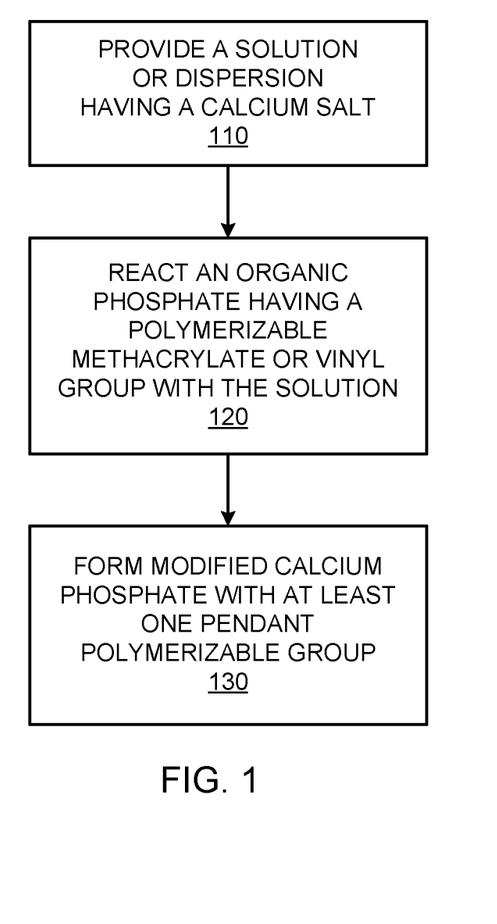
FIG. 1 is a flow chart showing a method of forming a modified calcium phosphate for use in adhesives suitable for dental and biomedical applications according to embodiments of the present invention.

FIG. 1 is a flow chart showing a method of forming a modified calcium phosphate (MCP) for use in adhesives suitable for dental or biomedical applications according to embodiments of the present invention. MCP is synthesized by the reaction of an organic phosphate source and a calcium salt. In step 110, a solution including a calcium salt is provided. The calcium salt may be dissolved in water, e.g., deionized water, or other suitable solvent. The calcium salt precursor used may be selected from various calcium sources, such as calcium chloride dehydrate, calcium hydroxide, calcium nitrate, and/or a mixture of calcium containing sources.

In step 120, the solution is reacted with an organic phosphate having at least one polymerizable methacrylate group, vinyl group or allyl group (the polymerizable organic phosphate source) in order to form a calcium phosphate having at least one pendant polymerizable group. The organic phosphate source may include Bis-2, methacryloyloxy ethyl phosphate, 10-methacryloyloxydecyl dihydrogen phosphate, glycerol dimethacrylate phosphate, glycerol monomethacrylate phosphate, triethyleneglycol methacrylate phosphate, methacryloyloxy propyl phosphate, methacryloyloxy hexyl phosphate, glyceryl phosphate, polyethylene glycol methacrylate phosphate, methacrylated aminomethyl phosphonic acid or other methacrylate esters or acrylate esters of polyethylene glycol mono phosphate, triethylene glycol monophosphate, triethyl phosphate, and/or inositol.

In step 130, modified calcium phosphate is formed. The structure and formation of the modified calcium phosphate depend on various parameters, such as the molar concentration and the ratios of the calcium and phosphate sources and the pH of the reaction medium as well as the temperature of the reaction medium. The calcium and phosphate ions form a varying number of salts such as mono calcium phosphates, dicalcium phosphates, tricalcium phosphates, tetracalcium phosphates based on the synthesis procedures such as ionic strength, pH and temperature. Hydroxyapatite is the most stable form of the calcium salts at physiological pH or above.

Restorative dental composites, including dental adhesives, often contain ethylenically unsaturated compounds with acid functionality, which includes monomers, oligomers and polymers having ethylenic unsaturation and/or acid precursor functionality. Prior art amorphous calcium phosphates are not stable in acidic conditions or in the presence of water. Therefore, resin formulations using such prior art calcium phosphates may result in the formation of unwanted salt formations with the acid functionality, which hinders their effective application. The modified calcium phosphate formed according to embodiments of the present invention is stable in acidic conditions and can actively take part in the polymerization reaction with other methacrylate functional groups. The modified calcium phosphate contains calcium and phosphate ions which are beneficial for the remineralization of the tooth and which can form an ionic bond with tooth structure and other bone-like structures.

The process of etching with phosphoric acid or other phosphate derivatives can result in the dissolution of superficial dental hard tissue and create micro-porosities on the tooth structure. An improper infiltration of the monomers into these micro-porosities can cause bond failures. These microporosities may further cause micro-leakage and sensitivity in the tooth. The calcium and phosphate present in the modified calcium phosphate formed according to embodiments of the present invention may have the ability to close these microporosities with precipitated calcium phosphate. This greatly improves the adhesive strength of the material to the tooth and the durability of the bond. The calcium containing modified calcium phosphate results in a strong ionic bond network. The presence of the modified calcium phosphate as a solubilized filler increases the strength and decreases polymerization shrinkage of dental compositions. Another advantage of the adhesive composition formed according to embodiments of the present invention is that the presence of the modified calcium phosphate enables remineralization of dentin and eventually should arrest any microleakage.

Figure 2:
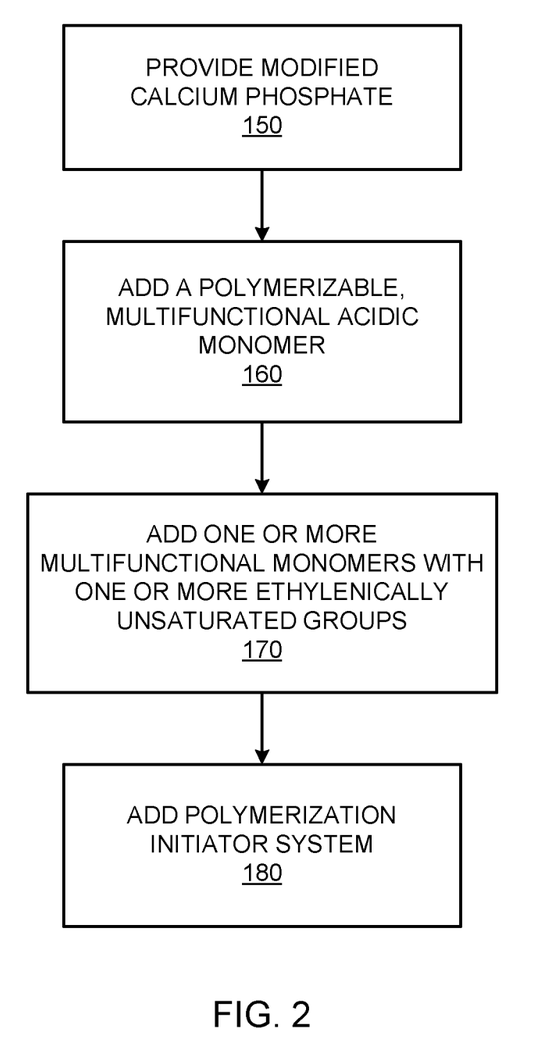
FIG. 2 is a flow chart showing a method of forming an adhesive composition according to embodiments of the present invention.

FIG. 2 is a flow chart showing a method of forming an adhesive composition according to embodiments of the present invention. In step 150, a modified calcium phosphate is provided, as described in FIG. 1. The amount of the modified calcium phosphate salt in the adhesive composition ranges from about 0.5%-50% by weight of the adhesive composition, preferably in the range of about 1%-50% wt %, and more preferably about 5-30 wt %. The composition of the adhesive can be adjusted so that modified calcium phosphate is completely soluble in the composition without the addition of any volatile solvent and forms a clear and transparent film on polymerization.

In step 160, a polymerizable, multifunctional acidic monomer having a concentration ranging from about 5% to about 45% by weight of the adhesive composition is added to the adhesive composition. Preferably, the acidic monomer is Bis-2, a dimethacrylate containing one covalently linked phosphoric acid group. Preferably, the amount of the acid functional monomers in the adhesive composition is sufficient to produce a pH in the range of about 1-4, as desired. The phosphoric acid monomer has the ability to etch the mineral phase of the dentin or other bone-like material and can form strong ionic bonds to dentin and other bone-like material. Phosphate containing monomers may include glycerol phosphate dimethacrylate, glycerol phosphate monomethacrylate, 10-methacryloyloxydecyl dihydrogen phosphate, methacryloyloxy ethyl phosphate, acryloyloxyethyl phosphate, dipentaaerythritol pentaacrylate phosphate, or vinyl phosphonic acid, and/or allyl phosphonic acid.

Embodiments of the adhesive composition may further include other acidic monomers such as carboxylic acid and/or sulfonic acid derivatives of acrylates, methacrylates and acrylamido derivatives. Carboxylic acid monomers may include acryloyl or methacryloyl derivatives maliec acid, succinic acid, phthalic acid, glyceroldimethacrylate-pyrromellitic acid and/or methacryloyloxyethyl trimellitic anhydride. Sulfonic acid monomers may include N-acrlyamido propyl sulfonic acid and/or methacryloyl derivatives of benzenesulfonic acid anhydride.

In step 170, one or more multifunctional monomers having one or more ethylenically unsaturated groups are added to the adhesive composition. The one or more multifunctional monomers have a concentration ranging from about 20% to about 60% by weight of the adhesive composition. For example, non-acidic monomer components may include methacrylate or acrylate functional monomers. Monofunctional methacrylates may include hydroxyl ethyl methacrylate, hydroxypropyl methacrylate, glycerol monomethacrylate, ethylene glycol mono methacrylate, and/or triethyleneglycol monomethacrylate. Preferably, the monofunctional methacrylate is hydroxyethyl methacrylate, which is hydrophilic and imparts wettability to the dentin. Preferably, the percentage of hydroxyethyl methacrylate may be in the range of about 2-15 wt. % of the adhesive composition. Too high a percentage of hydroxyl-functional monomers in the adhesive composition will make the composition more hydrophilic and susceptible to high water absorption. The mixture may further contain other multimethacrylate monomers, such as urethane dimethacrylate, 2,2-bis(4-(2-hydroxy 3-methacryloylpropoxy)-phenyl)propane (BisGMA), ethoxylated bisphenol-A dimethacrylate, biphenol-A dimethacrylate, 1, 6 hexamethylene dimethacrylate, polyethylene glycol dimethacrylate, triethylene glycol dimethacrylate, and/or trimethylolpropane trimethacrylate.

Embodiments of the adhesive composition may optionally include a volatile or non-volatile polar solvent, other than water, to facilitate greater penetration of the monomers into the dental tubules. The preferred polar solvents have good compatibility with the monomer composition and are miscible or soluble with water. Non-volatile polar solvents, those which provide greatest penetration into biological tissues, may include dimethyl sulfoxide (DMSO), dimethyl formamide (DMF), N-Methyl Pyrrolidinone (NMP), n-butanol and mixtures thereof. Volatile solvents are solvents which have high vapor pressure at ambient temperatures and a boiling point under the boiling point of water. Volatile solvents may include methanol, ethanol, acetone, isopropanol and/or a methyl ethyl ketone. The amount of volatile and non-volatile solvent in the adhesive composition may be varied depending upon the intended use.

Embodiments of the adhesive composition may optionally include water in the range of about 1-6 wt. % of the adhesive composition to facilitate etching. Though the presence of water increases the initial bond strength, adhesive formulations with water may lose structural and chemical integrity upon aqueous aging, unless the formulation is stabilized. See Spencer, Paulette et al.; "Adhesive Dentin Interface: The Weak Link in Composite Restoration," Ann. Biomed Eng., 2010 38(6) 1989-2003. The presence of the modified calcium phosphate in the adhesive composition serves to stabilize of the formulation and the integrity of the bond against aging. Embodiments of the present invention have excellent shelf life for a period of more than 24 months in the temperature range of 0° C. to 60° C.

Embodiments of the adhesive composition may further include fillers and other viscosity imparting materials when the adhesive composition is used, for example, as a nail polish or as an orthodontic bracket adhesive, among other possible uses. The fillers may be inorganic fillers such as micro- or nano-sized silica or alumina fillers and small particle glass fillers which do not affect the translucency of the adhesive composition. Other viscosity imparting materials that may be used are adhesive soluble, high molecular weight polymers or oligomers. Organic viscosity modifiers may further regulate the adhesive nature of the adhesive composition. Preferably, organic viscosity and adhesive modifiers include polyvinylidene difluoride, cellulose acetate, cellulose acetate propionate, cellulose acetate butyrate, carboxy methyl cellulose, polyvinyl pyrrolidinone, polybutanediol, polyesterdiols, and/or polyether diols. The organic fillers or additives may regulate the adhesive property of the formulation and also help to release the adhesive, if desired, by using suitable solvents in which the non-reactive fillers are soluble. Preferably, solvents used to de-bond the adhesive include ethanol, isopropanol, acetone, methyl ethyl ketone, propylene glycol, and/or glycerin.

In step 180, a polymerization initiator system is added to the adhesive composition. Preferably, the initiator system is a photoinitiator system, which typically includes of a photosensitizer and a reducing agent, such as an amine, e.g., a tertiary amine. A polymerizable composition which undergoes polymerization upon irradiation from a light source is referred to as a photopolymerizable composition. Preferably, the photoinitiator system includes Camphorquinone(CQ)/amine photoinitiator systems, where CQ is the photosensitizer. Preferably, the tertiary amines used in combination with CQ include Ethyl 4-(dimethylamino)benzoate and/or 2-(dimethylamino)ethyl methacrylate. Preferably, embodiments of the adhesive composition have an amount of amine reducing agent in the range of about 0.1 to 2 wt. % of the adhesive composition. Other photo initiators used for visible light curing photo-polymerization may include phosphate oxides, such as ethyl 2,4,6-trimethylbenzoyl-phenylphosphinate (TPO), also referred to by the tradename Lucirin (BASF Corp Charlotte, N.C.), and other acyl and multiacyl phosphine oxides, such as Irgacure 819, (Ciba Specialty Chemicals, Basel, Switzerland). A tertiary photoinitiator that may be used for the polymerization of acidic monomers is a diphenyl iodonium salt, such as diphenyl iodonium chloride.

EXAMPLES

A set of experiments were conducted to prove the viability of the adhesive composition formed according to embodiments of the present invention. Fourier Transform Infrared (FTIR) spectroscopy of the powdered samples and specimens were taken on a Nicolet IR 200 (ThermoFischer) machine in total attenuation reflective (ATR) mode. The samples were scanned in the spectral range of 4000-400 $cm^{-1}$. The samples were light cured using. an LE.Demetron II, a Light Emitting Diode curing light, with an output intensity of 1200 $mW/cm^2$. The shear strength measurements were taken using an Instron 1010 Universal Testing Machine (Instron, Canton, Mass., USA). Before measurements, the diameter of the bonded resin cylinder was measured using a digital caliper (Mitutoyo, Japan) to confirm the bonding area, and the interface was examined using magnification. Shear bond tests were carried out using an Ultradent (Utah, USA) jig with a crosshead speed of 1 mm/min.

Preparation of Modified Calcium Phosphate (MCP)

Figure 3:
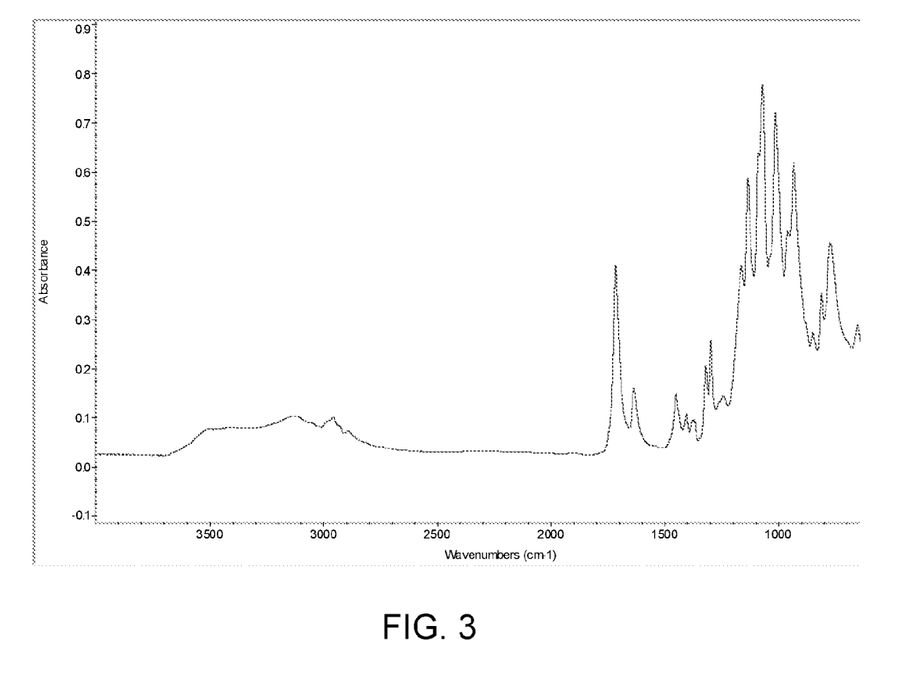
FIG. 3 is a graph showing an FTIR (ATR) spectrum of methacrylated calcium phosphate powder formed according to embodiments of the present invention.

The modified calcium phosphate was prepared by dissolving 111.6 g of calcium chloride dihydrate in 150 mL of deionized water and adding the solution to a one liter reactor vessel equipped with a mechanical stirrer, thermometer and a dropping funnel. To this solution, Bis-2 solution (231 g Bis-2 in 200 mL deionized water) was added gradually under constant and vigorous stirring. The temperature of the reaction was maintained at 40° C. The stirring was continued for 1 hour. To this solution, an ammonia solution (3%) was added slowly until the pH of the solution reached 9-10. The reaction was continued for another 4 hours and the temperature was maintained at 40° C. The precipitated methacrylated calcium phosphate was filtered out, washed thoroughly with deionized water to remove all residual ammonia solution and dried at 40° C. The yield of the reaction was about 75% (177 g). Analyzed on FTIR, MCP showed a C=C bond absorption peak at 1636 $cm^{-1}$, indicating the presence of polymerizable methacrylate groups. The FTIR spectrum is shown in FIG. 3, which shows 1716 $cm^{-1}$ (C=O); 1636 $cm^{-1}$ (C=C); 1320 $cm^{-1}$; 1136-1015 $cm^{-1}$ (C—O) and (Ca—O—P) peaks.

Polymerizability of MCP

Figure 4:
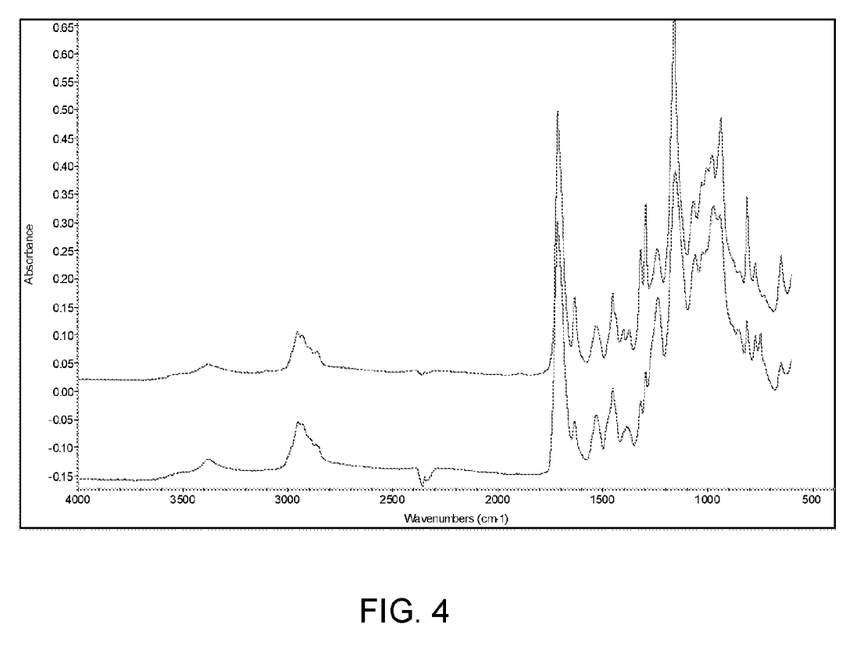
FIG. 4 is a graph showing an FTIR (ATR) spectrum of a dental adhesive showing its visible light curing polymerization (VLC) formed according to embodiments of the present invention.

In order to investigate the polymerizing ability of the solid methacrylated calcium phosphate with another methacrylated monomer, the curing of a mixture comprised of 50% MCP and 50% 2-hydroxyethyl methacrylate (HEMA), a mono-functional monomer, was tested. The test sample formed a solid, hard and translucent film on irradiation with a Demetron LE light for 20 seconds. This showed the polymerization ability of MCP and its cross-linking ability to a representative mono-functional monomer. HEMA forms a hard material only with multifunctional monomers. With mono-functional monomers, HEMA undergoes linear polymerization, resulting in a soft, flexible, soluble mass. The polymerization rate and kinetics were studied by ATR-FTIR spectroscopy. The FTIR spectrum is shown in FIG. 4. As shown in FIG. 4, the absorption intensity of the aliphatic C=C peak at 1642 $cm^{-1}$, which is present in the methacrylated calcium phosphate as well as the in the monomers, was decreased upon irradiation of the visible light. The upper line shows the absorption intensity before irradiation with visible light and the lower line shows the absorption intensity after irradiation with visible light showing the reduction in C=C peak absorption (1642 cm-1) on polymerization.

Calcium and Phosphate Ion Release Measurements

To determine calcium and phosphate ion release from the adhesive material, 15 mm diameter by 1 mm thick discs were fabricated in a silicon mold. The calcium and phosphate ion release from the discs in one day and seven days were determined by atomic absorption spectroscopy and colorimetric analysis, respectively. The material released 1624 µg of phosphate and 967 µg calcium ions per gram of material in 24 h and it released 2276 µg of phosphate ions and 1378 µg calcium ions per gram of material in seven days, both tests at pH 4.

Preparation of Teeth for Testing Shear Bond Strength to Dentin

After extraction, the teeth were stored in 10% histological formaldehyde solution. The teeth were cleaned to free them of soft tissue and embedded in circular acrylic matrices. The embedded teeth were then cut to remove the crown and ground flat. Prior to use, dentin surfaces were polished with 200 grit and 600 grit silicon-carbide sand papers.

Testing of Shear Bond Strength to Non-Etched Dentin

The polished dentin surfaces were blotted dry. The adhesive composition (formed according to the Examples below) was applied using a Micro-Brush (Micro-Brush, Grafton, Wis., USA) and was agitated for 10 seconds. The adhesive composition was then light cured for 10 seconds using a Optilux 150 curing light (Kerr, Calif., US). A dental composite disc (Showcase, Pulpdent Corp., USA) was applied over the substrate through an Ultradent bonding unit (Ultradent, Utah, USA) and mold, with an internal diameter of 2.38 mm. The composite was light cured for 40 seconds. The mold was removed and the composite was further light cured for additional 20 seconds. The sample specimens were then subjected to (i) immediate shear bond strength measurement; and (ii) shear bond strength measurement after storage in water for 24 hour. The immediate measurements were made for only few examples, but 24 h measurements (after storage in water) were made for all examples.

Testing of Shear Bond Strength on Etched Dentin

The polished dentin surfaces were etched with Etch-Rite (37% phosphoric acid gel, Pulpdent Corp., US) for 10 seconds, rinsed and then dried to free them of moisture. The adhesive composition (formed according to the Examples below) was applied using a Micro-Brush (Micro-Brush, Grafton, Wis., USA), agitated for 10 seconds and then light cured for 10 seconds using a Optilux 150 Curing light (Kerr, Calif., US). A dental composite disc (Showcase, Pulpdent Corp., USA) was then applied over the substrate through an Ultradent bonding unit (Ultradent, Utah, USA) and mold, with an internal diameter of 2.38 mm. The composite was light cured for 40 seconds. The mold was removed and the composite was further light cured for 20 seconds. The sample specimens were stored in water at 37° C. and then subjected to shear bond strength measurement after 24 h.

Example 1

24 parts MCP were mixed with 76 Wt. % Bis-2 to form a clear, thick paste. To this paste, 0.7 Wt. % 2-(dimethylamino)ethyl methacrylate (DMAEMA); 0.62% Ethyl 4-(dimethylamino)benzoate (E-4-DMAB) and 0.30 Wt. % Camphorquinone (CQ) were added and mixed at room temperature for 24 hours prior to bond testing. The formulation showed good bond strength to dry as well as wet dentin surfaces. Number of specimens used: 6.

Shear bond strength on non-Etched Dentin (Dry): 15.8 (3.8) MPa

Shear bond strength on non-Etched Dentin (Wet): 15.1 (4.8) MPa

Example 2

16 parts MCP were mixed with 51 Wt. % Bis-2 and 32 Wt. % urethane dimethacrylate (UDMA, Evonik) to form a clear, thick paste. To this paste, 0.73 Wt. % 2-(dimethylamino) ethyl methacrylate (DMAEMA); 0.61% Ethyl 4-(dimethylamino)benzoate (E-4-DMAB) and 0.34 Wt. % camphorquinone (CQ) were added and mixed at room temperature for 24 hours prior to bond testing. The formulation showed good bond strength to wet and dry dentin surfaces. Number of specimens used: 6.

Shear bond strength on non-Etched Dentin (Dry): 17.4 (2.9) MPa

Shear bond strength on non-Etched Dentin (Wet): 17.1 (4.3) MPa

Example 3

13 parts MCP were mixed with 40 Wt. % Bis-2, 25 Wt. % UDMA, and 22 Wt. % polyethylene glycol 600 dimethacrylate (PEG600DMA) to form a clear monomer mixture. To this mixture, 0.68 Wt. % DMAEMA; 0.6% E-4-DMAB and 0.31 Wt. % CQ were added and mixed at room temperature for 24 hours prior to bond testing. The formulation did not show good bond strength to wet and dry dentin surfaces. Number of specimens used: 6.

Shear bond strength on non-Etched Dentin (Dry): 7.0 (2.0) MPa

Shear bond strength on non-Etched Dentin (Wet) 8.8 (2.1) MPa

Example 4

A monomer composition including 30.97 Wt. % Bis-2, 30.97 Wt. % UDMA, 20.6 Wt. % 1,6-Hexamethylene dimethacrylate (HMDMA), 15.5 Wt. % 2-hydroxyethyl methacrylate (HEMA), 1.06 Wt. % DMAEMA, 0.64% E-4-DMAB and 0.35 Wt. % CQ was mixed at room temperature for 24 hours prior to bond testing.

Shear bond strength on non-Etched Dentin after storage at 37° C. in water for 24 hours: 11 (3.6) MPa

Example 5

3.45 parts MCP were mixed with a monomer composition including 29.9 Wt. % Bis-2, 29.9 Wt. % UDMA, 19.9 Wt. % HMDMA, and 14.4 Wt. % HEMA. To this mixture, 1.03 Wt. % DMAEMA, 0.61 Wt. % E-4-DMAB, 0.34 Wt. % CQ were added and mixed overnight prior to bond testing.

Shear bond strength on non-Etched Dentin after storage at 37° C. in water for 24 hours: 14 (3.8) MPa Shear bond strength on Etched Dentin after storage at 37° C. in water for 24 hours: 19 (4.1) MPa

Example 6

8.55 parts MCP were mixed with a monomer composition including 28.1 Wt. % Bis-2, 28.0 Wt. % UDMA, 19.1 Wt. % HMDMA, and 14.07 Wt. % HEMA. To this mixture, 0.9 Wt. % DMAEMA, 0.52 Wt. % E-4-DMAB, 0.31 Wt. % CQ were added and mixed overnight prior to bond testing.

Shear bond strength on non-Etched Dentin after storage at 37° C. in water for 24 hours: 15.2 (3.2) MPa Shear bond strength on Etched Dentin after storage at 37° C. in water for 24 hours: 22.5 (4.6) MPa

Example 7

16.8 parts MCP were mixed with a monomer composition including 25.8 Wt. % Bis-2, 25.8 Wt. % UDMA, 18.0 Wt. % HMDMA, and 11.06 Wt. % HEMA. To this mixture, 0.9 Wt. % DMAEMA, 0.54 Wt. % E-4-DMAB, and 0.31 Wt. % CQ were added and mixed overnight prior to bond testing.

Shear bond strength on non-Etched Dentin after storage at 37° C. in water for 24 hours: 21.0 (5.6) MPa Shear bond strength on Etched Dentin after storage at 37° C. in water for 24 hours: 32.0 (6.5) MPa

Example 8

24.5 parts MCP were mixed with a monomer composition including 23.7 Wt. % Bis-2; 23.7, Wt. % UDMA, 16.63 Wt. % HMDMA, and 10.5 Wt. % HEMA. To this mixture, 0.85 Wt. % DMAEMA, 0.52 Wt. % E-4-DMAB, and 0.29 Wt. % CQ were added and mixed overnight prior to bond testing.

Shear bond strength on non-Etched Dentin after storage at 37° C. in water for 24 hours: 22.0 (5.6) MPa Shear bond strength on Etched Dentin after storage at 37° C. in water for 24 hours: 32.0 (6.0) MPa

Example 9

11.5 parts MCP were mixed with a monomer composition including 28.7 Wt. % Bis-2; 28.7, Wt. % UDMA, 20.0 Wt. % HMDMA, and 8.6 Wt. % HEMA and 2.5 wt. % 10-Methacryloyloxydecyl dihydrogen phosphate (10-ten) CAS #85590-00-7. To this mixture, 0.85 Wt. % DMAEMA, 0.52 Wt. % E-4-DMAB, and 0.29 Wt. % CQ were added and mixed overnight prior to bond testing.

Shear bond strength on non-Etched Dentin after storage at 37° C. in water for 24 hours: 21.75 (1.5) MPa Shear bond strength on Etched Dentin after storage at 37° C. in water for 24 hours: 25.8 (4.7) MPa

Example 10

11.0 parts MCP were mixed with a monomer composition including 27.4 Wt. % Bis-2; 27.4 Wt. % UDMA; 19.2 Wt. % HMDMA; 8.3 Wt. % HEMA; 4 wt. % 10-ten and 2.6 Wt. % water. To this mixture, 0.85 Wt. % DMAEMA, 0.52 Wt. % E-4-DMAB, and 0.29 Wt. % CQ were added and mixed overnight prior to bond testing.

Shear bond strength on non-Etched Dentin after storage at 37° C. in water for 24 hours: 23 (5.6) MPa Shear bond strength on Etched Dentin after storage at 37° C. in water for 24 hours: 25.4 (5.5) MPa Effect of Adding Solvents to Formulations Example 11a 0.6 grams of the adhesive formulation of Example 7 were added with 0.4 grams of acetone to make a bonding agent formulation with 40 Wt. % acetone. The shear bond strength of the bonding agent was measured as described above.

Shear bond strength on non-Etched Dentin after storage at 37° C. in water for 24 hours: 20.0 (3.6) MPa Shear bond strength on Etched Dentin after storage at 37° C. in water for 24 hours: 27.2 (6.0) MPa Example 11b 1.2 grams of the adhesive formulation of Example 5 were added with 0.8 grams of acetone to make a bonding agent formulation with 40 Wt. % acetone. The shear bond strength of the bonding agent was measured as described above.

Shear bond strength on non-Etched Dentin after storage at 37° C. in water for 24 hours: 17.8 (3.2) MPa Shear bond strength on Etched Dentin after storage at 37° C. in water for 24 hours: 25.0 (2.0) MPa Example 11c 2.0 grams of the adhesive formulation of example 6 were added with 0.2 grams ethanol to make a formulation with 10 Wt. % ethanol. The shear bond strength of the bonding agents was measured as described above.

Shear bond strength on non-Etched Dentin after storage at 37° C. in water for 24 hours: 18.2 (4.8) MPa Shear bond strength on Etched Dentin after storage at 37° C. in water for 24 hours: 25.0 (6.0) MPa Example 11d 2.6 grams of the adhesive formulation of example 4 were added with 0.26 grams acetone to make a formulation with 10 Wt. % acetone. The shear bond strength of the bonding agents was measured as described above.

Shear bond strength on non-Etched Dentin after storage at 37° C. in water for 24 hours: 18.2 (4.8) MPa Shear bond strength on Etched Dentin after storage at 37° C. in water for 24 hours: 28.4 (6.0) MPa Example 11e 16.1 parts MCP were mixed with a monomer composition including 24.8 Wt. % Bis-2, 24.8 Wt. % UDMA, 17.3 Wt. % HMDMA, 10.6 Wt. % HEMA and 4 Wt. % distilled water. To this mixture, 0.9 Wt. % DMAEMA, 0.54 Wt. %, 0.31 Wt. % CQ were added and mixed overnight prior to bond testing.

Shear bond strength on non-Etched Dentin after storage at 37° C. in water for 24 hours: 19.3 (2.8) MPa Shear bond strength on Etched Dentin after storage at 37° C. in water for 24 hours: 27.2 (3.2) MPa Examples of Use as a Nail Coating Formulation Example 12a An adhesive composition having 25 parts Bis-2; 40 parts UDMA, 20 parts HMDMA and 5 parts Trimethylolpropane trimethacrylate was mixed with 10 parts MCP to make a homogeneous, clear mixture. Curing chemistry was added to the composition by mixing 10 grams of the resin mixed with 0.03 grams CQ, 0.06 grams DMAEMA and 0.06 grams E-4-DMAB. The formulation was then applied to a fingernail and cured with visible light as described above with a Demetron LE light for 20 seconds. A high gloss surface resulted. The nail polish remained in place without cracking, chipping, swelling or showing other signs of deterioration for more than one month. The nail polish was very hard to remove using a solvent or a nail polish remover.

Example 12b

The removability of the nail polish was enhanced by the addition of a monomer soluble polymer to the above formulation. 6 parts of the nail coating formulation of Example 7 were mixed with 1 part of cellulose acetate butyrate. Application of the coating on the nail generated a high gloss surface on irradiation with a visible light for 20 seconds. The nail polish could be removed by soaking the nail polish with a tissue soaked with acetone or a nail polish remover.

DISCUSSION

Adhesive formulations with methacrylated calcium phosphate exhibited good bond strength. Example 1 represents a formulation only containing Bis-2, its calcium salt (MCP) and the initiator system. Though this formulation exhibited comparatively good bond strength to non-etched dentin, high water absorption and the high acidic nature of the formulation is detrimental to the long term stability of a restoration fabricated from the material. Examples 2 and 3 illustrate adhesive compositions without the use of low molecular weight, hydrophilic monomer, 2-hydroxyethyl methacrylate. Example 3, with polyethylene glycol as the hydroxyl functional monomer, yielded much lower bond strength values. As the amount of MCP in the adhesive formulation is increased, the shear bond strength also improves (see Examples 4 through 8). A small addition of the long-chain, phosphate monomer 10-Methacryloyloxydecyl dihydrogen phosphate (10-ten) CAS #85590-00-7 to the formulation significantly improves the bond strength of the composition (see Examples 9 and 10). 10-ten forms much stronger covalent bonds with the calcium ions present in tooth structure. The effect of various volatile solvents and water in the adhesive formulations were also studied (see Examples 11a through 11e), and their effect was not found to be significant. Use of the MCP formulation as a coating for nails was examined in Examples 12a and 12b.

As part of the etch-and-rinse procedure in dentistry, the aggressive phosphoric acid nearly completely deprives collagen of apatite. In the oral environment, the presence of MCP formed according to embodiments of the present invention may replenish the calcium deprived collagen and close the nanometer-sized channels along the collagen fibrils within the hybrid layer, although other mechanisms may be possible.

Although the above discussion discloses various exemplary embodiments of the invention, it should be apparent that those skilled in the art may make various modifications that will achieve some of the advantages of the invention without departing from the true scope of the invention.

What is claimed is:

1. An adhesive composition for bonding to bone and bone-like structures, the composition comprising:
   a polymerizable, multifunctional acidic monomer having a concentration ranging from 23% to about 45% by weight of the adhesive composition;
   one or more multifunctional non-acidic monomers with one or more ethylenically unsaturated groups, the one or more multifunctional monomers having a concentration ranging from about 20% to about 60% by weight of the adhesive composition;
   an organically modified calcium phosphate salt having a concentration ranging from about 1% to about 50% by weight of the adhesive composition, the modified calcium phosphate salt having one or more pendant polymerizable methacrylate groups; and
   a polymerization initiator system.

2. The adhesive composition of claim 1, wherein the multifunctional acidic monomer is bis[2-(methacryloyloxy)ethyl] phosphate, glycerol dimethacrylate phosphate, ethylene glycol methacrylate phosphate, polyethylene glycol methacrylate phosphate, methacryloyl ethyl oxy polycaprolactone phosphate, allyl phosphate, vinyl phosphonic acid, 2-Acrylamido-2-methylpropanephosphonic acid, methacryloyloxy decyl hydrogen phosphate, methacryloyloxy ethyloxy phosphate, 10-methacryloyloxydecyl dihydrogen phosphate, or a combination thereof.

3. The adhesive composition of claim 1, wherein the organically modified calcium phosphate salt has a concentration ranging from about 23% to about 30% by weight of the adhesive composition.

4. The adhesive composition of claim 1, wherein the organically modified calcium phosphate salt is completely soluble in the adhesive composition.

5. The adhesive composition of claim 1, wherein the organically modified calcium phosphate salt is stabilized by a reaction of a calcium salt and an organically functional phosphate monomer having at least one polymerizable group.

6. The adhesive composition of claim 5, wherein the organically functional phosphate monomer is bis[2-(methacryloyloxy)ethyl] phosphate or vinyl phosphonic acid and bis[2-(methacryloyloxy)ethyl] phosphate.

7. The adhesive composition of claim 1, wherein the polymerization initiator system has a concentration ranging from about 0.1% to about 4% by weight.

8. The adhesive composition of claim 1, wherein the polymerization initiator system includes a photo-polymerization initiator having a concentration ranging from about 0.25% to about 3% by weight of the adhesive composition.

9. The adhesive composition of claim 1, further comprising a volatile organic solvent having a concentration ranging from about 0.1% to about 40% by weight of the adhesive composition.

10. The adhesive composition of claim 1, further comprising one or more inert fillers, wherein the inert fillers include glass, quartz, silica or combinations thereof.

11. The adhesive composition of claim 1, further comprising one or more non-polymerizable, polymeric fillers that regulate adhesive property of the adhesive composition when using one or more solvents in which the one or more non-polymerizable, polymeric fillers are soluble.

12. The adhesive composition of claim 11, wherein the one or more non-polymerizable, polymeric fillers are polyvinylidene difluoride, cellulose acetate, cellulose acetate propionate, cellulose acetate butyrate or a combination thereof.

13. A method of forming an adhesive composition for bonding to bone and bone-like structures for use in dental or biomedical applications, the method comprising:
   providing an organically modified calcium phosphate salt having a concentration ranging from about 1% to about 50% by weight of the adhesive composition, the modified calcium phosphate salt having one or more pendant polymerizable methacrylate groups;
   adding a polymerizable, multifunctional acidic monomer having a concentration ranging from 23% to about 45% by weight of the adhesive composition;
   adding one or more multifunctional non-acidic monomers with one or more ethylenically unsaturated groups, the one or more multifunctional monomers having a concentration ranging from about 20% to about 60% by weight of the adhesive composition; and
   adding a polymerization initiator system.

14. The method of claim 13, wherein the multifunctional acidic monomer is bis[2-(methacryloyloxy)ethyl] phosphate, glycerol dimethacrylate phosphate, ethylene glycol methacrylate phosphate, polyethylene glycol methacrylate phosphate, methacryloyl ethyl oxy polycaprolactone phosphate, allyl phosphate, vinyl phosphonic acid, 2-Acrylamido-2-methylpropanephosphonic acid, methacryloyloxy decyl hydrogen phosphate, methacryloyloxy ethyloxy phosphate, 10-methacryloyloxydecyl dihydrogen phosphate, or a combination thereof.

15. The method of claim 13, wherein the organically modified calcium phosphate salt has a concentration ranging from about 23% to about 30% by weight of the adhesive composition.

16. The method of claim 13, wherein the organically modified calcium phosphate salt is completely soluble in the adhesive composition.

17. The method of claim 13, wherein the organically modified calcium phosphate salt is stabilized by a reaction of a calcium salt and an organically functional phosphate monomer having at least one polymerizable group.

18. The method of claim 17, wherein the organically functional phosphate monomer is bis[2-(methacryloyloxy)ethyl] phosphate or vinyl phosphonic acid and bis[2-(methacryloyloxy)ethyl] phosphate.

19. The method of claim 13, wherein the polymerization initiator system has a concentration ranging from about 0.1% to about 4.0% by weight.

20. The method of claim 13, wherein the polymerization initiator system includes a photo-polymerization initiator having a concentration ranging from about 0.25% to about 3% by weight of the adhesive composition.

21. The method of claim 13, further comprising:
   adding a volatile organic solvent having a concentration ranging from about 0.1% to about 40% by weight of the adhesive composition.

22. The method of claim 13, further comprising:
   adding one or more non-polymerizable, polymeric fillers that regulate adhesive property of the adhesive composition when using one or more solvents in which the one or more non-polymerizable, polymeric fillers are soluble.

23. The method of claim 22, wherein the one or more non-polymerizable, polymeric fillers are polyvinylidene difluoride, cellulose acetate, cellulose acetate propionate, cellulose acetate butyrate, carboxy methyl cellulose, polyvinyl pyrrolidinone, polybutanediol, polyesterdiols, polyether diols or combinations thereof.

* * * * *